United States Patent
Bosques et al.

(10) Patent No.: US 10,023,894 B2
(45) Date of Patent: *Jul. 17, 2018

(54) GALACTOSE-ALPHA-1, 3-GALACTOSE-CONTAINING N-GLYCANS IN GLYCOPROTEIN PRODUCTS DERIVED FROM CHO CELLS

(71) Applicant: Momenta Pharmaceuticals, Inc., Cambridge, MA (US)

(72) Inventors: Carlos J. Bosques, Arlington, MA (US); Jennifer Murphy, Marshfield, MA (US); Hetal Sarvaiya, Quincy, MA (US); Nathaniel Washburn, Littleton, MA (US); Cuihua Liu, Belmont, MA (US); Xiao-Jin Xu, Southborough, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 180 days.

This patent is subject to a terminal disclaimer.

(21) Appl. No.: 14/832,784

(22) Filed: Aug. 21, 2015

(65) Prior Publication Data

US 2016/0053292 A1 Feb. 25, 2016

Related U.S. Application Data

(63) Continuation of application No. 14/056,674, filed on Oct. 17, 2013, which is a continuation of application
(Continued)

(51) Int. Cl.
*C12P 21/00* (2006.01)
*G01N 33/53* (2006.01)
*C07K 14/705* (2006.01)

(52) U.S. Cl.
CPC ...... *C12P 21/005* (2013.01); *C07K 14/70521* (2013.01); *G01N 33/5308* (2013.01);
(Continued)

(58) Field of Classification Search
CPC ............ C12P 21/005; C07K 14/70521; C07K 2319/30; G01N 33/5308; G01N 2400/02;
(Continued)

(56) References Cited

U.S. PATENT DOCUMENTS 5,143,854 A 9/1992 Pirrung et al.
5,288,514 A 2/1994 Ellman
(Continued)

FOREIGN PATENT DOCUMENTS

JP 2007-292690 A 11/2007
WO WO-91/19502 A1 12/1991
(Continued)

OTHER PUBLICATIONS

Smith et al. Transfer and Expression of a Murine UDP Gal:β-D-Gal-α1, 3-Galactosyltransferase Gene in Transfected Chinese Hamster Ovary Cells, The Journal of Biological Chemistry 265 (11): 6225-6234 (Apr. 15, 1990).*
(Continued)

*Primary Examiner* — Gailene Gabel
(74) *Attorney, Agent, or Firm* — Choate, Hall & Stewart LLP; Rolando Medina; Stephanie L. Schonewald

(57) ABSTRACT

Methods of producing recombinant therapeutic fusion proteins described herein can include culturing Chinese hamster ovary (CHO) cells under conditions suitable for expression of a recombinant therapeutic fusion protein including one or more glycans, where the CHO cells have not been genetically engineered to produce terminal alpha-galactosyl residues on glycans; treating the one or more glycans of the recombinant glycoprotein with one or more exoglycosi-
(Continued)

dases; measuring glycans containing terminal galactose-alpha-1-3-galactose residues on the fusion protein by nuclear magnetic resonance (NMR); and producing a recombinant therapeutic fusion protein in the CHO cells if a target level of terminal galactose-alpha-1-3-galactose residues is measured.

17 Claims, 7 Drawing Sheets

Related U.S. Application Data

No. 12/529,109, filed as application No. PCT/US2009/031678 on Jan. 22, 2009, now Pat. No. 8,586,356.

(52) U.S. Cl.
CPC ...... C07K 2319/30 (2013.01); G01N 2400/02 (2013.01); Y10T 436/24 (2015.01); Y10T 436/25 (2015.01); Y10T 436/25125 (2015.01); Y10T 436/25375 (2015.01)

(58) Field of Classification Search
CPC ........... Y10T 436/25375; Y10T 436/24; Y10T 436/25125; Y10T 436/25
See application file for complete search history.

(56) References Cited

U.S. PATENT DOCUMENTS

| | | | |
|---|---|---|---|
| 5,384,261 A | 1/1995 | Winkler et al. | |
| 5,510,270 A | 4/1996 | Fodor et al. | |
| 5,527,681 A | 6/1996 | Holmes | |
| 5,695,937 A | 12/1997 | Kinzler et al. | |
| 5,871,997 A | 2/1999 | Rother et al. | |
| 8,586,356 B2 * | 11/2013 | Bosques ............ | G01N 33/5308 435/208 |
| 2011/0045496 A1 | 2/2011 | Bosques et al. | |
| 2014/0045212 A1 | 2/2014 | Bosques et al. | |

FOREIGN PATENT DOCUMENTS

| | | |
|---|---|---|
| WO | WO-93/22684 A1 | 11/1993 |
| WO | WO-02/099089 A1 | 12/2002 |
| WO | WO-2006/002243 A2 | 1/2006 |
| WO | WO-2007/115813 A1 | 10/2007 |
| WO | WO-2008/028686 A2 | 3/2008 |
| WO | WO-2008/130926 A2 | 10/2008 |
| WO | WO-2010/085251 A1 | 7/2010 |

OTHER PUBLICATIONS

Annex 1, Summary of Product Characteristics, Enbrel 25 mg powder and solvent for solution for injection, 2 pages.
Cho, S.K., and Cummings, R.D., A Soluble Form of a1,3-Galactosyltransferase Functions within Cells to Galactosylate Glycoproteins, Journal of Biological Chemistry, 272 (21): 13622-13626 (1997).
Raju, T. S., Glycosylation Variations with Expression Systems and their impact on Biological Activity of Therapeutic Immunoglobulins, BioProcess International, 44-53 (2003).
Zamze, S. et al., Glycosylation of a CNS-specific extracellular matrix glycoprotein, tenascin-R is dominated by O-linked sialylated glycans and "brain type" neutral N-glycans, Glycobiology, 9(8): 823-831 (1999).
Anumula, K.R., Advances in Fluorescence Derivatization Methods for High-Performance Liquid Chromatographic Analysis of Glycoprotein Carbohydrates, Anal. Biochem., 350(1):1-23 (2006).
Ashford, D.A. et al., Site-specific Glycosylation of Recombinant Rat and Human Soluble CD4 Variants Expressed in Chinese Hamster Ovary Cells, The Journal of Biological Chemistry, 268(5):3260-3267 (1993).
Baker, K.N., et al., Metabolic control of recombinant protein N-glycan processing in NS0 and CHO cells, Biotechnol. Bioeng., 73:188-202 (2001).
Beck, A. et al., Trends in glycosylation, glycoanalysis and glycoengineering of therapeutic antibodies and Fc-fusion proteins, Curr. Pharm. Biotechnol., 9:482-501 (2008).
Benton, T. et al., The use of UCOE vectors in combination with a preadapted serum free, suspension cell line allows for rapid production of large quantities of protein, Cytotechnology, 38: 43-46 (2002).
Bhindi, R. et al., Brothers in arms: DNA enzymes, short interfering RNA, and the emerging wave of small-molecule nucleic acid-based gene-silencing strategies, Am. J. Pathol., 171(4):1079-88 (2007).
Bosques et al., Addendum: Chinese hamster ovary cells can produce galactose-alpha-1,3 galactose antigens on proteins, Nature Biotechnology, 29(5):459 (2011).
Bosques, C.J., et al., Chinese hamster ovary cells can produce galactose-α-1, 3-galactose antigens on proteins, Nature Biotechnology, 28(11):1153-1156 (2010).
Carr, S.A. et al., Protein and carbohydrate structural analysis of a recombinant soluble CD4 receptor by mass spectrometry, J. Biol. Chem., 264:21286-21295 (1989).
Chung, C.H. et al., Cetuximab-Induced Anaphylaxis and IgE Specific for Galactose-α-1,3-Galactose, N. Engl. J. Med., 358:1109-1117 (2008).
Davidson, D.J. et al., Oligosaccharide structures present on asparagine-289 of recombinant human plasminogen expressed in a Chinese hamster ovary cell line, Biochemistry, 30:625-633 (1991).
Defrancq, L. et al., High-Throughput Analysis of the N-Glycans of NS0 Cell-Secreted Antibodies, BioProcess International, 60-62, 64, 66 and 68 (2004).
Déglon, N. et al., Presence of Gal-alpha 1, 3Gal epitope on xenogeneic lines: implications for cellular gene therapy based on the encapsulation technology, Xenotransplantation, 10(3):204-213 (2003).
Galili, U. et al., Evolutionary relationship between the natural anti-Gal antibody and the Gal alpha 1----3Gal epitope in primates, Proceedings of the National Academy of Sciences, 84:1369-1373 (1987).
Hara, S. et al., Determination of Mono-O-acetylated N-Acetylneuraminic Acids in Human and Rat Sera by Fluorometric High-Performance Liquid Chromatography, Anal. Biochem., 179:162-166 (1989).
Hong, J.K. et al., Substitution of glutamine by glutamate enhances production and galactosylation of recombinant IgG in Chinese hamster ovary cells, Appl. Microbiol. Biotechnol., 88:869-876 (2010).
International Search Report for PCT/US2009/031678, dated Jun. 2, 2009.
Jefferis, R., Glycosylation as a strategy to improve antibody-based therapeutics, Nat. Rev. Drug Discov., 8:226-234 (2009).
Jefferis, R., Glycosylation of Recombianant Antibody Therapeutics, CCE IX: Review, Biotechnology Progress, 21: 11-16 (2005).
Jenkins, N. et al., Getting the glycosylation right: implications for the biotechnology industry, Nat. Biotechnol., 14:975-981 (1996).
Kagawa, Y. et al., Comparative study of the asparagine-linked sugar chains of natural human interferon-beta 1 and recombinant human interferon-beta 1 produced by three different mammalian cells, J. Biol. Chem., 263:17508-17515 (1988).
Kumpel, B.M. et al., Galactosylation of human IgG monoclonal anti-D produced by EBV-transformed B-lymphoblastoid cell lines is dependent on culture method and affects Fc receptor-mediated functional activity, Hum. Antibodies Hybridomas, 5:143-151 (1994).
Lai, L. et al., Production of α-1,3-Galactosyltransferase Knockout Pigs by Nuclear Transfer Cloning, Science, 295:1089-1092 (2002).
Lin, S.S. et al., Differential recognition by preoteins of α-galactosyl rediues on endothelial cell surfaces, Glycobiology, 8(5):461-471 (1998).

(56) References Cited

OTHER PUBLICATIONS

Liu, J. et al., Anti-pig antibody adsorption efficacy of {alpha}-Gal carrying recombinant P-selectin glycoprotein ligand-1/immunoglobulin chimeras increases with core 2 {beta}1, 6-N-acetylglucosaminyltransferase expression, Glycobiology, 15(6): 571-583 (2005).

Macher, B.A. and Galili, U., The Galalpha1,3Galbeta1,4GlcNAc-R (alpha-Gal) epitope: a carbohydrate of unique evolution and clinical relevance, Biochim. Biophys. Acta, 1780:75-88 (2008).

McCamish, M., Advisory committee for pharmaceutical science and clinical pharmacology (ACPS-CP), FDA ACPS-CP Update on Biosimilars, FDA White Oaks Conference Center, Silver Spring, MD, Aug. 8, 2012, (Presentation): slides 1,14 and 16 (2012).

Pan, W. et al., Antisense applications for biological control, J. Cell Biochem., 98(1):14-35 (2006).

Parekh, R.B. et al., N-glycosylation and in vitro enzymatic activity of human recombinant tissue plasminogen activator expressed in Chinese hamster ovary cells and a murine cell line, Biochemistry, 28:7670-7679 (1989).

Potvin, B. et al., Transfection of a Human alpha-(1,3) Fucosyltransferase Gene into Chinese Hamster Ovary Cells. Complications arise from activation of endogenoius alpha-(1,3) fucosyltransferases, The Journal of Biological Chemistry, 265(3):1615-1622 (1990).

Sasaki et al., Carbohydrate structure of erythropoietin expressed in Chinese hamster ovary cells by a human erythropoietin cDNA, J. Biol. Chem., 262:12059-12076 (1987).

Shah, P.S. et al., Active site studies of bovine alpha1 → 3-galactosyltransferase and its secondary structure prediction, Biochim Biophys Acta, 1480(1-2):222-234 (2000).

Sheeley, D.M., et al., Characterization of Monoclonal Antibody Glycosylation: Comparison of Expression Systems and Identification of Terminal α-Linked Galactose, Analytical Biochemistry, 247(1):102-10 (1997).

Sioud, M. et al., Ribozymes, DNAzymes and small interfering RNAs as therapeutics, Curr. Drug Targets, 6(6):647-53 (2005).

Smith, D.F. et al., Transfer and Expression of a Murine UDP-Gal:β-D-Gal-alpha1, 3-Galactosyltransferase Gene in Transfected Chinese Hamster Ovary Cells, The Journal of Biological Chemistry, 265(11):6225-6234 (1990).

Spellman, M.W. et al., Carbohydrate structures of human tissue plasminogen activator expressed in Chinese hamster ovary cells, J. Biol. Chem., 264:14100-14111 (1989).

Spellman, M.W. et al., Carbohydrate structures of recombinant soluble human CD4 expressed in Chinese hamster ovary cells, Biochemistry, 30:2395-2406 (1991).

Srinivas, N.R. et al., Assessment of Dose Proportionality, Absolute Bioavailability, and Immunogenicity Response of CTLA4Ig (BMS-188667), a Novel Immunosuppressive Agent, Following Subcutaneous and Intravenous Administration of Rats, Pharm. Res., 14(7):911-6 (1997).

Srinivas, N.R. et al., Pharmacokinetics and Pharmacodynamics of CTLA4Ig (BMS-188667), a Novel Immunosuppressive Agent, in Monkeys Following Multiple Doses, J. Pharm. Sci., 85(1):1-4 (1996).

Stadlmann, J. et al., Analysis of Immunoglobulin Glycosylation by LC-ESI-MS of Glycopeptides and Oligosaccharides, Proteomics, 8(14):2858-71 (2008).

Takeuchi, M. et al., Comparative study of the asparagine-linked sugar chains of human erythropoietins purified from urine and the culture medium of recombinant Chinese hamster ovary cells, J. Biol. Chem., 263:3657-3663 (1988).

Takeuchi, M. et al., Relationship between sugar chain structure and biological activity of recombinant human erythropoietin produced in Chinese hamster ovary cells, Proc. Natl. Acad. Sci. USA, 86:7819-7822 (1989).

Taylor, S.G. et al., Characterization of the rat alphs(1,3)galactosyltransferase: evidence from two independent genes encoding glycosylatransferases that syntheseize Gal alpha(1,3)Gal by two separate glycosylation pathways, Glycobiology, 13:327-337 (2003).

Townsend, R.R., Carbohydrate Analysis, High Performance Liquid Chromatography and Capillary Electrophoresis., Ed. Z. El Rassi, pp. 181-209 (1995).

Urlaub, G. and Chasin, L.A., Isolation of Chinese Hamster Cell Mutants Deficient in Dihydrofolate Reductase Activity, PNAS, 77(7):4216-4220 (1980).

Van Berkel, P.C. et al., N-linked glycosylation is an important parameter for optimal selection of cell lines producing biopharmaceutical human IgG, Biotechnology Progress, 25:244-251 (2009).

Weiner, R.S., et al., A Sensitive Enzyme Immunoassay for the Quantitation of Human CTLA4Ig Fusion Protein in Mousse Serum: Pharmacokinetic Application to Optimizing Cell Line Selection, J. Pharm. Biomed. Anal., 15(5):571-9 (1997).

Written Opinion of the International Searching Authority to PCT/US2009/031678, dated Jun. 2, 2009.

Wurm, F.M., Production of recombinant protein therapeutics in cultivated mammalian cells, Nature Biotech., 22:1393-1398 (2004).

Yamane-Ohnuki, N. et al., Esablishment of FUT8 Knockout Chinese Hamster Ovary Cells: An Ideal Host Cell Line for Producing Completely Defucosylated Antibodies With Enhanced Antibody-Dependent Cellular Cytotoxicity, Biotechnol. Bioeng., 87:614-622 (2004).

Yuen, C. et al., The spectrum of N-linked oligosaccharide structures detected by enzymic microsequencing on a recombinant soluble CD4 glycoprotein from Chinese hamster ovary cells, Eur. J. Biochem., 192:523-528 (1990).

\* cited by examiner

GALACTOSE-ALPHA-1, 3-GALACTOSE-CONTAINING N-GLYCANS IN GLYCOPROTEIN PRODUCTS DERIVED FROM CHO CELLS

This application is a continuation of U.S. application Ser. No. 14/056,674, filed Oct. 17, 2013, now abandoned, which is a continuation of U.S. application Ser. No. 12/529,109, filed Nov. 10, 2010, now U.S. Pat. No. 8,586,356, which was the National Stage of International Application No. PCT/US09/31678, filed Jan. 22, 2009, the entire contents of each of which are incorporated herein by reference.

FIELD OF THE INVENTION

The present invention relates to methods and materials for the detection of particular glycan structures in proteins expressed from mammalian cell expression systems.

BACKGROUND OF THE INVENTION

Many recombinant therapeutic biopharmaceutical products are produced in mammalian cell cultures such as Chinese Hamster Ovary (CHO) cells. Mammalian cell cultures are preferred over other expression systems such as yeast and prokaryotic systems for the production of recombinant glycoproteins, largely because the mammalian cell cultures produce glycoproteins with glycosylation patterns that are generally recognized and tolerated by humans.

The potentially adverse effects of terminal alpha-linked galactose (gal-α-1,3-gal) linkages are known Chung et al., N Engl J Med, 358:11 (2008). It has been previously reported that such terminal alpha-gal linkages are not present in recombinant glycoproteins produced by Chinese Hamster Ovary (CHO) cells. For example, while an anti-CDw52 antibody, Campath, produced in NSO, a murine-developed myeloma cell line, includes potentially immunogenic glycoforms having nonreducing terminal alpha-linked galactose residues, Campath produced from CHO cells contained primarily three glycoforms which are consistent with normal human IgG. Sheeley et al., Analytical Biochemistry 247: 102-110 (1997).

SUMMARY OF THE INVENTION

The present invention is based, in part, on the discovery that glycoproteins produced from recombinant CHO cells contain glycan structures with terminal galactose-α-1,3-galactose linkages, which can have deleterious effects on the use of such glycoproteins for therapeutic purposes. For example, administration of glycoproteins with terminal alpha-gal linkages to humans for therapeutic purposes can lead to the formation of monoclonal antibodies to the recombinant glycoprotein in patients, such that subsequent administrations will be less effective or even cause adverse hypersensitivity reactions in the patient.

Contrary to this previous teaching, Applicants have surprisingly found that a significant fraction of recombinant glycoproteins produced in CHO cell cultures may exhibit the presence of terminal gal-α-1,3-gal linkages, presenting the potential for adverse reactions to protein and peptidyl products administered to patients.

The present invention provides compounds and methods which are useful for the production and analysis of recombinant glycoproteins from CHO cells and compositions containing such glycoproteins, wherein the glycoproteins comprise modulated (e.g., reduced or, in some cases, increased) levels of terminal gal-α-1,3-gal linkages.

Thus, in a first aspect, the present invention comprises methods for evaluating a Chinese Hamster Ovary (CHO) cell population. In certain embodiments, the testing method includes:

(a) providing one or more CHO cells from the population; and (b) measuring glycans containing terminal galactose-alpha-1-3-galactose residues produced by said cells, wherein the CHO cells have not been genetically engineered to express an alpha-galactosyl transferase coding sequence.

The measuring step may include any of the following: (a) isolating glycoproteins produced by the cells and measuring the glycans containing terminal galactose-alpha-1-3-galactose residues on the glycoproteins, (b) isolating a specific glycoprotein composition produced by the cells and measuring the glycans containing terminal galactose-alpha-1-3-galactose residues on the isolated glycoprotein composition, (c) isolating glycans from glycoproteins produced by the cells and measuring the glycans containing terminal galactose-alpha-1-3-galactose residues in the isolated glycans, (d) cleaving monosaccharides from glycans present on the glycoprotein or the one or more CHO cells, and detecting the terminal released alpha-galactose residues from the cleaved monosaccharides, (e) providing at least one peptide from a glycoprotein produced by the cells, and measuring the glycans containing terminal galactose-alpha-1-3-galactose residues on the at least one peptide, (f) measuring a relative level of glycans containing terminal galactose-alpha-1-3-galactose residues on the glycoprotein by measuring glycans on the cell surface of the one or more CHO cells. The technique used to measure terminal gal-α-1,3-gal linkages can include one or more of the following methods, and combinations of any of these methods: chromatographic methods, mass spectrometry (MS) methods, electrophoretic methods (such as capillary electrophoresis), nuclear magnetic resonance (NMR) methods, monosaccharide analysis, fluorescence methods, UV-VIS absorbance, enzymatic methods, and use of a detection molecule (such as an antibody or lectin).

The source of glycans for the measuring of step 2 may be selected from the group consisting of the population of CHO cells; glycoproteins or glycans expressed at the surface of the CHO cells; peptides derived from the cleavage of proteins present on the surface of the cells of the population of CHO cells; glycans present on the surface of the population of CHO cells; glycoproteins secreted or expressed by the population of CHO cells, an isolated glycoprotein expression product expressed from a CHO cell or population of CHO cells; peptides derived from the isolated protein expression product expressed from a CHO cell or population of CHO cells; or glycans derived from the isolated protein expression product expressed from a CHO cell or directly from a population of CHO cells. In some embodiments, the method includes treating a source of glycans or glycopeptides with one or more exoglycosidase, including an alpha-galactosidase enzyme, followed by analysis of the glycan population.

In some embodiments, the method used provides a quantitative measure of glycans containing terminal galactose-alpha-1-3-galactose residues. In some embodiments, the method used provides a qualitative measure.

In some embodiments, the method also includes preparing a glycoprotein preparation from a culture of the CHO cells, cleaving one or more glycans from the glycoprotein preparation (e.g., with one or more glycosidases such as α-1,3- galactosidases; α-1,4-galactosidases; or α-1,6-galactosidases), and measuring the glycans containing terminal galactose-alpha-1-3-galactose residues.

In certain embodiments, the method is conducted during a production run for a therapeutic glycoprotein by obtaining a sample from the CHO cell culture of the production line, e.g., to monitor glycan structure during production. In certain embodiments, the measuring step is repeated at least once over time, e.g., the measuring step is repeated at least once, twice, three times or more, during the time period of culture of the CHO cells. In other embodiments, the method is conducted on a glycoprotein product produced from CHO cells, e.g., as part of a quality or release testing of the glycoprotein product.

In some embodiments, the measuring step includes comparing the level of glycans containing terminal galactose-alpha-1-3-galactose residues in a first glycoprotein preparation produced from a first population of CHO cells to the level of glycans containing terminal galactose-alpha-1-3-galactose residues in a second glycoprotein preparation produced from a second population of CHO cells. In some such embodiments, glycans of a glycoprotein preparation from populations of CHO cells cultured under different culture conditions are determined and compared.

In some embodiments, the method may further comprise a step of comparing the level of glycans containing terminal galactose-alpha-1-3-galactose residues to a reference level (e.g., to a control level, or to a range or value in a product specification).

In certain embodiments of the method the measuring step includes use of a detection molecule which is able to detect the presence or absence of terminal alpha-galactosyl residues. In certain embodiments, the detection molecule comprises an antibody that is able to bind to terminal alpha-galactosyl epitopes. In other embodiments of the invention, the detection molecule comprises a lectin. In some embodiments, the detection molecule may comprise a fluorescent moiety, or a radioisotope moiety.

The CHO cell population may comprise a clonal cell population. The CHO cell population may be in culture, e.g., or a sample from a cell culture in a bioreactor for manufacturing a therapeutic glycoprotein. In certain embodiments, the CHO cell population will have been transformed with at least one vector encoding a therapeutic glycoprotein. The therapeutic glycoprotein may be of human, non-human or synthetic origins. The therapeutic glycoprotein may be for treatment of humans or veterinary indications.

In some embodiments, the method further includes a step of evaluating a biological activity of the glycoprotein produced by the cell, e.g., evaluating the presence or level of immunogenic potential of the glycoprotein, e.g., in vitro or in vivo, e.g., in an animal model.

In a second aspect, the invention comprises methods for screening one or more Chinese Hamster Ovary (CHO) cells for the ability to produce glycans containing terminal galactose-alpha-1-3-galactose residues on a glycoprotein, the method comprising:

(a) providing a plurality of CHO cell populations wherein none of the plurality have been genetically engineered to produce terminal alpha-galactosyl residues on glycans (e.g., have not been genetically engineered to express an alpha-galactosyl transferase coding sequence);

(b) culturing each of the plurality of CHO cells under conditions suitable for expression of a glycoprotein expression product;

(c) measuring glycans containing terminal galactose-alpha-1-3-galactose residues produced by each of the plurality of CHO cells, and (d) selecting one or more of the plurality of CHO cell preparations based on the presence of a target level of terminal galactose-alpha-1-3-galactose residues produced by the selected CHO cell preparation.

The glycans containing terminal galactose-alpha-1-3-galactose residues may be obtained and measured from glycoproteins produced by the CHO cell preparations, from an isolated glycoprotein expression product of the CHO cell preparations, from peptides obtained from a glycoprotein expression product of the CHO cell preparations, from cell surface glycans of the CHO cell preparations, or from glycan preparations obtained from the CHO cell preparations or from a glycoprotein expression product thereof. In certain embodiments, the screening method further comprises the step of isolating a glycoprotein expression product from the cell culture and measuring the terminal galactose-alpha-1-3-galactose residues on a glycoprotein produced by the cells in step (c). In certain embodiments, the cell screening method further comprises the step of quantifying the amount of alpha-galactosyl residues present on the glycoprotein expression product. In certain embodiments, step (b) of the cell screening method takes place in a bioreactor.

Each of the plurality of CHO cell populations may comprise a different CHO strain population, a different clonal cell population, or different samples (e.g., samples taken over time) from a cell culture in a manufacturing train for a therapeutic glycoprotein. In certain embodiments, the CHO cell population will have been transformed with at least one vector encoding a therapeutic glycoprotein, e.g., a human therapeutic glycoprotein. In certain embodiments of the cell screening method, the glycoprotein expression product is a secreted glycoprotein expressed from the CHO cells.

The measuring step of the screening method may include any technique disclosed herein for identifying and/or quantifying terminal alpha-galactosyl residues on a glycoprotein.

In a third aspect, the invention includes a method for evaluating a glycoprotein composition produced in a CHO cell host. The method includes measuring the amount of terminal galactose-alpha-1-3-galactose present in a glycoprotein composition, wherein the glycoprotein composition was produced in CHO host cells, and wherein the CHO host cells were not genetically engineered to express an alpha-galactosyl transferase coding sequence.

In some embodiment, the method includes recording the level of terminal galactose-alpha-1-3-galactose present in the glycoprotein composition in a print or computer-readable medium.

In some embodiments, the method also includes comparing the measured level of terminal galactose-alpha-1-3-galactose present in the glycoprotein composition with a reference level, such as a control or reference specification. The reference level can be a specification (e.g., an FDA label or Physician's Insert) or quality criterion for a pharmaceutical preparation containing the glycoprotein composition.

In some embodiment, the reference level or quality criterion is no more than 5% terminal galactose-alpha-1-3-galactose present in a glycoprotein composition, e.g., no more than 4.5%, 4%, 3.5%, 3%, 2.5%, 2%, 1.5%, 1%, 0.5%, 0.25%, 0.2%, 0.1% or less. The level of galactose-alpha-1-3-galactose present in a glycoprotein composition can be measured as the level of glycans containing galactose-alpha-1-3-galactose relative to total amount of glycans in a sample, such as a glycoprotein preparation.

In one embodiment, the technique used to measure terminal gal-α-1,3-gal linkages includes a chromatographic method.

In one embodiment, the technique used to measure terminal gal-α-1,3-gal linkages includes mass spectrometry (MS) methods.

In one embodiment, the technique used to measure terminal gal-α-1,3-gal linkages includes electrophoretic methods (such as capillary electrophoresis).

In one embodiment, the technique used to measure terminal gal-α-1,3-gal linkages includes nuclear magnetic resonance (NMR) methods.

In one embodiment, the technique used to measure terminal gal-α-1,3-gal linkages includes monosaccharide analysis.

In one embodiment, the technique used to measure terminal gal-α-1,3-gal linkages includes fluorescence methods.

In one embodiment, the technique used to measure terminal gal-α-1,3-gal linkages includes UV-VIS absorbance.

In one embodiment, the technique used to measure terminal gal-α-1,3-gal linkages includes enzymatic methods.

In one embodiment, the technique used to measure terminal gal-α-1,3-gal linkages includes and use of a detection molecule (such as an antibody or lectin).

DEFINITIONS

Figure 1:
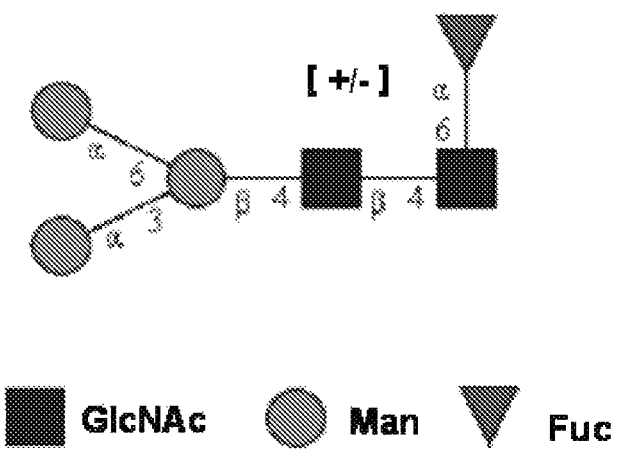
FIG. 1 is a representation of the core pentasaccharide common to N-glycan structures.

Unless otherwise defined hereinbelow, all terms used herein are used in their ordinary meaning, as would be understood by one skilled in the art.

Approximately, About, Ca.: As used herein, the terms "approximately", "about" or "ca.," as applied to one or more values of interest, refer to a value that is similar to a stated reference value. In certain embodiments, the terms "approximately", "about" or "ca.," refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less of the stated reference value.

Detection, Detecting: As used herein, the terms "detecting," "detection" and "detecting means" are used interchangeably to refer to the determination of whether a particular chemical moiety, such as a terminal alpha-1,3-galactosyl residue, is present or absent in or on a compound, composition, cell or cell population. The detecting means may involve a selectable marker, or an identifiable characteristic such as a fluorescent or radioactive moiety, and may involve labeling of a reagent, compound, cell or cell population. Detection can also refer to the analysis of a compound, composition, cell or cell population, using such techniques as mass spectrometry or related methods, electrophoretic methods, nuclear magnetic resonance, chromatographic methods, or combinations of the above, to determine the presence or absence of a chemical moiety in or on a compound, composition, cell or cell population. Detection may also involve quantification of the absolute or relevant levels of the chemical moiety being detected.

Glycan: As is known in the art and used herein "glycans" are sugars. Glycans can be monomers or polymers of sugar residues, but typically contain at least three sugars, and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'sulfo N-acetylglucosamine, etc.). The term "glycan" includes homo and heteropolymers of sugar residues. The term "glycan" also encompasses a glycan component of a glycoprotein (e.g., of a glycoprotein, glycolipid, proteoglycan, etc.). The term also encompasses free glycans, including glycans that have been cleaved or otherwise released from a glycoprotein.

Glycan preparation: The term "glycan preparation" as used herein refers to a set of glycans obtained according to a particular production method. In some embodiments, glycan preparation refers to a set of glycans obtained from a glycoprotein preparation (see definition of glycoprotein preparation below). In some embodiments, a glycan preparation includes glycoproteins. In some embodiments, a glycan preparation includes released glycans.

Glycoprotein: As used herein, the term "glycoprotein" refers to a "protein" (as defined herein) that contains a peptide backbone covalently linked to one or more sugar moieties (i.e., glycans). As is understood by those skilled in the art, the peptide backbone typically comprises a linear chain of amino acid residues. The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. In certain embodiments, sugar moieties may include sulfate and/or phosphate groups. Alternatively or additionally, sugar moieties may include acetyl, glycolyl, propyl or other alkyl modifications. In certain embodiments, glycoproteins contain O-linked sugar moieties; in certain embodiments, glycoproteins contain N-linked sugar moieties.

Glycoprotein preparation: A "glycoprotein preparation," as that term is used herein, refers to a set of individual glycoprotein molecules, each of which comprises a polypeptide having a particular amino acid sequence (which amino acid sequence includes at least one glycosylation site) and at least one glycan covalently attached to the at least one glycosylation site. Individual molecules of a particular glycoprotein within a glycoprotein preparation typically have identical amino acid sequences but may differ in the occupancy of the at least one glycosylation sites and/or in the identity of the glycans linked to the at least one glycosylation sites. That is, a glycoprotein preparation may contain only a single glycoform of a particular glycoprotein, but more typically contains a plurality of glycoforms. Different preparations of the same glycoprotein may differ in the identity of glycoforms present (e.g., a glycoform that is present in one preparation may be absent from another) and/or in the relative amounts of different glycoforms.

Glycosidase: The term "glycosidase" as used herein refers to an agent that cleaves a covalent bond between sequential sugars in a glycan or between the sugar and the backbone moiety (e.g., between sugar and peptide backbone of glycoprotein). In some embodiments, a glycosidase is an enzyme. In certain embodiments, a glycosidase is a protein (e.g., a protein enzyme) comprising one or more polypeptide chains. In certain embodiments, a glycosidase is a chemical cleavage agent, e.g., hydrazine.

N-glycan: The term "N-glycan," as used herein, refers to a polymer of sugars that has been released from a glycoprotein but was formerly linked to a glycoprotein via a nitrogen linkage (see definition of N-linked glycan below).

N-linked glycans: N-linked glycans are glycans that are linked to a glycoprotein via a nitrogen linkage. A diverse assortment of N-linked glycans exists, but is typically based on the common core pentasaccharide $(Man)_3(GlcNAc)(GlcNAc)$.

O-glycan: The term "O-glycan," as used herein, refers to a polymer of sugars that has been released from a glycoconjugate but was formerly linked to the glycoconjugate via an oxygen linkage (see definition of O-linked glycan below).

O-linked glycans: O-linked glycans are glycans that are linked to a glycoconjugate via an oxygen linkage. O-linked glycans are typically attached to glycoproteins via N-acetyl-D-galactosamine (GalNAc) or via N-acetyl-D-glucosamine (GlcNAc) to the hydroxyl group of L— serine (Ser) or L-threonine (Tlir). Some O-linked glycans also have modifications such as acetylation and sulfation.

Modulate: The term "modulate" as used herein refers to the ability to of an actor to control, within prescribed limits, the value of a parameter, such as the level of alpha-galactose residues present in a glycoprotein composition. Thus, in some embodiments, the level of alpha-galactose residues may be modulated so that it remains within prescribed limits. In some embodiments, the level of alpha-galactose residues may be modulated so that it does not exceed more than 5.0%, 1.0%, 0.5%, 0.1%, 0.05% or 0.01% of the total N-glycans present in a glycoprotein composition. In other embodiments, the level of alpha-galactose residues may be modulated so that it does not vary by more than 10.0%, 5.0%, 1.0%, 0.5% or 0.1% of a prescribed or desired level.

Protease: The term "protease" as used herein refers to an agent that cleaves a peptide bond between sequential amino acids in a polypeptide chain. In some embodiments, a protease is an enzyme (i.e., a proteolytic enzyme). In certain embodiments, a protease is a protein (e.g., a protein enzyme) comprising one or more polypeptide chains. In certain embodiments, a protease is a chemical cleavage agent.

Providing: The term "providing" as used herein refers to an actor obtaining a subject item, such as a CHO cell, CHO cell preparation, or glycoprotein preparation, from any source including, but not limited to, obtaining by the actor's own manufacture or by the actor's receiving the item from another party. For example, a CHO cell preparation is provided if it is made or received by any machine, person, or entity. In some embodiments, a CHO cell preparation may be received by a machine, which may then perform one or more tests, processes, or refinements of the glycoprotein preparation. In some embodiments, a CHO cell preparation may be received by a person. In some embodiments, a CHO cell preparation may be received from an outside entity. In some embodiments, a CHO cell preparation may be received by a person or business performing characterization services for a second person or business.

Figure 2:
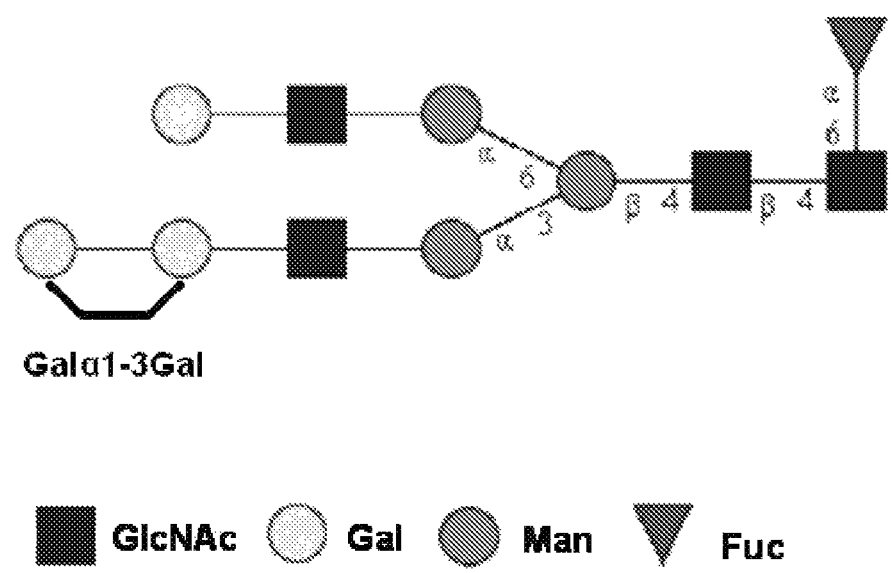
FIG. 2 is a representation of the non-reducing end N-glycan structure having a terminal gal-α-1,3-gal linkage.

Terminal $\alpha$-1,3-galactose residue; terminal gal-$\alpha$-1,3-gal linkage: The terms "terminal $\alpha$-1,3-galactose residue," "terminal gal-$\alpha$-1,3-gal linkages" and "non-reducing end $\alpha$-1,3 linked galactose residue" as used herein, interchangeably describe the glycan structure illustrated in FIG. 2, in which a glycan structure that may be attached to a peptide or protein terminates with two galactose residues that are bound to each other at the residues denominated as the 1, and 3 residues, respectively, on the galactose molecules.

DETAILED DESCRIPTION OF CERTAIN EMBODIMENTS

Although host cells used for the synthesis of recombinant glycoproteins possess the intracellular machinery to produce complex glycosylation, these cells do not always possess the same complement of enzymes as the cells in which the glycoprotein is naturally expressed. Clonal selection of cell lines and variations in manufacturing conditions may also produce heterogeneity in glycoproteins expressed in cultured cells. The functional role of glycosylation in glycoprotein activity necessitates careful characterization of therapeutic products produced in cell lines.

It has been previously reported that terminal gal-$\alpha$-1,3-gal linkages are not present in recombinant glycoproteins produced by Chinese Hamster Ovary (CHO) cells. Chung et al., N Engl J Med, 358:11 (2008). The present disclosure is based, at least in part, on the unexpected finding that terminal $\alpha$-1,3-galactose residues can be found on glycoproteins produced by CHO cells, and thus it is important to identify, monitor and control this aspect of glycan structure when using CHO cells to produce therapeutic products.

The present disclosure provides methods of analyzing the composition of glycans on glycoproteins produced by CHO cells. According to the present disclosure, glycans from glycoprotein preparations produced in CHO cells can be analyzed to determine whether they include terminal $\alpha$-1,3-galactose residues. The present disclosure provides methods of detecting such modifications, and methods of producing glycoproteins that include or lack such modifications.

Glycan Preparations

The present disclosure provides methods of analyzing the structure and/or composition of individual glycans within a glycan preparation, e.g., evaluating glycans containing terminal galactose-alpha-1-3-galactose residues produced by CHO cells, e.g., evaluating terminal alpha-galactosyl residues on glycoproteins produced by CHO cells. A glycan preparation may be obtained from a cell preparation or a from a glycoprotein by any method available in the art. In general, obtaining a glycan preparation comprises steps of (1) obtaining a cell or glycoprotein preparation; and (2) optionally releasing glycans from the cell or glycoprotein preparation. In some embodiments, obtaining a glycan preparation optionally comprises labeling the glycan preparation with a detectable label.

Glycoprotein Preparations

Methods for recombinant production of glycoproteins have been described.

Glycoproteins secreted by cultured cells can be isolated and purified by any available means, such as anion-exchange chromatography, reversed-phase chromatography, gel filtration, immunoaffinity chromatography, and combinations thereof.

N-Linked Glycan Preparation

In some embodiments, an N-glycan preparation is obtained by providing a glycoprotein population and removing N-linked glycans from the glycoproteins in the population.

In some embodiments, N-linked glycans are removed from glycoproteins (e.g., glycoproteins) by digestion. Generally, glycanases to be used in accordance with the present disclosure cleave between GlcNAc-Asn, GlcNAc-GlcNAc, or Man-GlcNAc residues of the core. Exemplary enzymes which can be used to remove N-linked glycans from glycoproteins include, but are not limited to, N-glycanase F and/or N-glycanase-A, O-glycanase and/or Endo H.

In some embodiments, N-linked glycans are removed from glycoproteins by chemical cleavage. To give but a few examples, hydrazine, sodium borohydride, and/or trifluoromethanesulfonic acid (TFMS) can be used to remove glycans from a glycoprotein.

O-linked Glycan Preparation

In some embodiments, an O-linked glycan preparation is obtained by providing a glycoprotein (e.g., glycoprotein) population and removing O-linked glycans from glycoproteins in the population.

In some embodiments, O-linked glycans are removed from glycoproteins (e.g., glycoproteins) by b-elimination. In some embodiments, O-linked glycans are removed from glycoproteins (e.g., glycoproteins) by reductive b-elimination. In some embodiments, O-glycans are removed from glycoproteins (e.g., glycoproteins) by non-reductive b-elimination.

In some embodiments, O-linked glycans are removed from a glycoprotein (e.g., a glycoprotein) preparation by incubating the preparation in a solution that includes alkaline tetrahydroborate. In some embodiments, tetradeuterioborate is used, e.g., to incorporate a deuterium label to facilitate detection of O-linked glycans. In various exemplary methods, a glycoprotein preparation is incubated in a solution containing 0.8-1.0 M $NaBH_4$ and 0.05-0.1 M NaOH at 42-45° C. for 2-24 hours. A reaction to remove O-linked glycans can be terminated by the addition of acid (e.g., 1.0 M HCl).

In some embodiments, O-linked glycans are removed from a glycoprotein preparation by incubating the preparation in a solution that includes NaOH. In various exemplary methods, a glycoprotein is incubated in a solution containing 50-200 mM NaOH at 27-45° C. for 2-48 hours. A reaction can be terminated by the addition of acid.

In some embodiments, O-linked glycans are removed from a glycoprotein preparation by incubating the preparation in a solution that includes $NH_4OH$. In various exemplary methods, a glycoprotein is incubated in a solution containing 25-28% $NH_4OH$ at 45-60° C. for 2-40 hours. The reaction can be terminated by removing the $NH_4OH$ under vacuum. In some embodiments, the solution includes ammonium carbonate (e.g., at a saturating concentration). In some embodiments, the $NH_4OH$-treated preparation is treated with acid (e.g., boric acid).

In some embodiments, O-linked glycans are removed from a glycoprotein preparation by incubating the preparation in an aqueous solution that includes ethylamine (e.g., ethylamine at about 70%) or methylamine (e.g., methylamine at about 40%), for about 4-24 hours.

In some embodiments, an O-linked glycan preparation is obtained from a glycoprotein population from which N-linked glycans have been removed.

Labeling Glycans

In some embodiments, labels can be associated with glycans before or after release from a glycoprotein. N-linked glycans or O-linked glycans (e.g., N-glycans that have been removed from a glycoprotein population) can be associated with one or more detectable labels. Detectable labels are typically associated with the reducing ends of glycans. In some embodiments, detectable labels are fluorescent moieties. Exemplary fluorophores that can be used in accordance with the present disclosure include, but are not limited to, 2-aminobenzoic acid (2AA), 2-aminobenzamide (2AB), and/or 2-aminopurine (2AP). In general, fluorophores for use in accordance with the present disclosure are characterized by having reactivity with the reducing end of an oligosaccharide and/or monosaccharide under conditions that do not damage and/or destroy the glycan. In some embodiments, fluorescent moieties are attached to reducing ends directly. For example, direct attachment can be accomplished by direct conjugation by reductive amination. In some embodiments, fluorescent moieties are attached to reducing ends indirectly. For example, indirect attachment can be accomplished by a reactive linker arm.

In some embodiments, detectable labels comprise radioactive moieties or isotopically-labelled molecules. Exemplary radioactive moieties that can be used in accordance with the present disclosure include, but are not limited to, tritium ($^3H$), deuterium ($^2H$), and/or $^{35}S$. Typically, such moieties are directly attached to or otherwise associated with the fluorophore. To give but one example of a radioactive fluorophore, 2AP can be modified such that all hydrogens are deuterated.

Release of Glycans

The present disclosure provides improved methods of determining glycosylation patterns of glycoproteins. Such methods can involve subjecting a glycan population to one or more exoglycosidases and analyzing the structure and/or composition of the digestion products. In some embodiments, exoglycosidases used in accordance with the present disclosure recognize and cleave only one particular type of glycosidic linkage. In some embodiments, exoglycosidases used in accordance with the present disclosure recognize and cleave more than one particular type of glycosidic linkage. Among the exoglycosidases which may be useful for the present invention are α-galactosidases, β-galactosidases; hexosaminidases, mannosidases; and combinations thereof, as described in Table 1.

Exoglycosidases

Exoglycosidases are enzymes which cleave terminal glycosidic bonds from the non-reducing end of glycans. They are typically highly specific to particular monosaccharide linkages and anomericity (α/β). In some embodiments, neighboring branching patterns can affect exoglycosidase specificity. Exoglycosidase treatment usually results in glycans of standard antennary linkages being cleaved down to the pentasaccharide core (M3N2) containing 3 mannose and 2 GlcNAc residues. However, unusually-modified species (e.g., antennary or core fucosylated species, high-mannose and hybrid glycans, lactosamine-extended glycans, sulfated glycans, phosphorylated glycans, etc.) are resistant to exoglycosidase treatment and can be chromatographically resolved and quantified relative to the M3N2 pentasaccharide.

Exemplary exoglycosidases that can be used in accordance with the present disclosure include, but are not limited to, sialidase, galactosidase, hexosaminidase, fucosidase, and mannosidase. Exoglycosidases can be obtained from any source, including commercial sources or by isolation and/or purification from a cellular source (e.g., bacteria, yeast, plant, etc.).

In some embodiments, exoglycosidases (e.g., sialidases, galactosidases, hexosaminidases, fucosidases, and mannosidases) can be divided into multiple categories or "subsets." In some embodiments, the different subsets display different abilities to cleave different types of linkages. Table 1 presents some exemplary exoglycosidases, their linkage specificities, and the organism from which each is derived. One of ordinary skill in the art will appreciate that this is an exemplary, not a comprehensive, list of exoglycosidases, and that any exoglycosidase having any linkage specificity may be used in accordance with the present disclosure.

structure and/or function of glycans in one glycoprotein preparation from one source to structure and/or function of glycans in at least one other glycoprotein preparation from another source. In some embodiments, the analysis comprises comparing the structure and/or function of glycans in one or more of the samples to structure and/or function of glycans in a reference sample.

Structure and composition of glycans can be analyzed by any available method. In some embodiments, glycan structure and composition are analyzed by chromatographic methods, mass spectrometry (MS) methods, chromatographic methods followed by MS, electrophoretic methods, electrophoretic methods followed by MS, nuclear magnetic resonance (NMR) methods, and combinations thereof.

In some embodiments, glycan structure and composition can be analyzed by chromatographic methods, including but

TABLE 1

Exoglycosidases

| Enzyme class | EC #* | Activity | Organism |
|---|---|---|---|
| α-Sialidase | 3.2.1.18 | α-2/3,6,8 (usually not linkage-specific) | *Arthrobacter ureafaciens*<br>*Vibrio cholerae*<br>*Clostridium perfringens* |
| | | α-2,3 (NeuAc from oligosaccharides) | *Salmonella typhimurium*<br>*Streptococcus pneumonia* |
| | | α-2/3,6 (NeuAc from complex) | *Clostridium perfringens* |
| β-Galactosidase | 3.2.1.23 | β-1/3,4,6 Gal linkages | Bovine testis<br>*Xanthamonas* species<br>*Streptococcus* species<br>*E. coli* |
| | | β-1/4,6 Gal linkages | Jack bean |
| | | β-1,4 Gal linkage | *Streptococcus pneumonia* |
| | | β-1,3-Gal linkage | *E. coli*<br>*Xanthomonas* species |
| | | β-1/3,6-Gal linkages | *Xanthomonas* species<br>*E. coli* |
| β-Hexosaminidase | 3.2.1.52<br>3.2.1.30 | β-1/2,3,4,6 hexosamines | *Streptococcus plicatus*<br>*Streptococcus pneumonia*<br>Bacteroides<br>Jack bean |
| α-Fucosidase | 3.2.1.51<br>3.2.1.111 | α-1-3,4-Fuc (usually de-glycosylate Lewis structure) | *Xanthomonas*<br>Almond meal |
| | | α-1/2,3,4,6-Fuc (usually has broad specificity) | Bovine kidney |
| | | α-1,6-Fuc | *C. meningosepticum* |
| | | α-1,2-Fuc | *E. coli*<br>*Xanthomonas* |
| α-Mannosidase | 3.2.1.24 | α-1/2,3,6-Man | Jack bean |
| | | α-1/2,3-Man | *Xanthomonas manihotis* |
| | | α-1,6-Man (typically a core mannosidase) | *Xanthomonas* species |
| | | α-1,2-Man | *Aspergillus saitoi* |
| β-Mannosidase | 3.2.1.25 | α-1,4-Man | *Helix pomatia* |

*"EC #" refers to Enzyme Commission registration number

According to the present disclosure, a glycan population can be digested with any exoglycosidase or any set of exoglycosidases. In general, exoglycosidase reactions take place under conditions that are compatible with enzyme activity. For example, pH, temperature, reaction solution components and concentration (e.g., salt, detergent, etc.), and length of reaction time can be optimized in order to achieve a desired level of exoglycosidase activity. See, e.g., WO 2008/130926, the contents of which are herein incorporated by reference.

Analysis of Glycan Structure and Activity

In general, methods in accordance with the disclosure comprise subjecting a glycan preparation to analysis to determine whether the glycan includes a particular type of modification (e.g., terminal α-1,3-galactose residues). In some embodiments, the analysis comprises comparing the not limited to, liquid chromatography (LC), high performance liquid chromatography (HPLC), ultra performance liquid chromatography (UPLC), thin layer chromatography (TLC), amide column chromatography, and combinations thereof.

In some embodiments, glycan structure and composition can be analyzed by mass spectrometry (MS) and related methods, including but not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof.

In some embodiments, glycan structure and composition can be analyzed by electrophoretic methods, including but not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof.

In some embodiments, glycan structure and composition can be analyzed by nuclear magnetic resonance (NMR) and related methods, including but not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

In some embodiments, techniques described herein may be combined with one or more other technologies for the detection, analysis, and or isolation of glycans or glycoproteins. For example, in certain embodiments, glycans are analyzed in accordance with the present disclosure using one or more available methods (to give but a few examples, see Anumula, *Anal. Biochem.* 350(1):1, 2006; Klein et al., *Anal. Biochem.* 179:162, 1989; and/or Townsend, R. R. Carbohydrate Analysis" High Performance Liquid Chromatography and Capillary Electrophoresis., Ed. Z. El Rassi, pp 181-209, 1995, each of which is incorporated herein by reference in its entirety). For example, in some embodiments, glycans are characterized using one or more of chromatographic methods, electrophoretic methods, nuclear magnetic resonance methods, and combinations thereof. Exemplary such methods include, for example, NMR, mass spectrometry, liquid chromatography, 2-dimensional chromatography, SDS-PAGE, antibody staining, lectin staining, monosaccharide quantitation, capillary electrophoresis, fluorophore-assisted carbohydrate electrophoresis (FACE), micellar electrokinetic chromatography (MEKC), exoglycosidase or endoglycosidase treatments, and combinations thereof. Those of ordinary skill in the art will be aware of other techniques that can be used to characterize glycans together with the methods described herein.

In some embodiments, methods described herein allow for detection of glycan species (such as terminal alpha-galactosyl residues) that are present at low levels within a population of glycans. For example, the present methods allow for detection of glycan species that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, or less than 0.01% within a population of glycans.

In some embodiments, methods described herein allow for detection of particular structures (e.g., terminal alpha-galactosyl residues) that are present at low levels within a population of glycans. For example, the present methods allow for detection of particular structures that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, or less than 0.01% within a population of glycans.

In some embodiments, methods described herein allow for detection of relative levels of individual glycan species within a population of glycans. For example, the area under each peak of a liquid chromatograph, can be measured and expressed as a percentage of the total. Such an analysis provides a relative percent amount of each glycan species within a population of glycans. In another example, relative levels of individual glycan species are determined from areas of peaks in a 1D-NMR experiment, or from volumes of cross peaks from a 1H-15HSQC spectrum (e.g., with correction based on responses from standards), or by relative quantitation by comparing the same peak across samples.

In some embodiments, a biological activity of a glycoprotein preparation (e.g., a glycoprotein preparation) is assessed. Biological activity of glycoprotein preparations can be analyzed by any available method. In some embodiments, a binding activity of a glycoprotein is assessed (e.g., binding to a receptor). In some embodiments, a therapeutic activity of a glycoprotein is assessed (e.g., an activity of a glycoprotein in decreasing severity or symptom of a disease or condition, or in delaying appearance of a symptom of a disease or condition). In some embodiments, a pharmacologic activity of a glycoprotein is assessed (e.g., bioavailability, pharmacokinetics, pharmacodynamics). For methods of analyzing bioavailability, pharmacokinetics, and pharmacodynamics of glycoprotein therapeutics, see, e.g., Weiner et al., J Pharm Biomed Anal. 15(5):571-9, 1997; Srinivas et al., J. Pharm. Sci. 85(1):1-4, 1996; and Srinivas et al., Pharm. Res. 14(7):911-6, 1997.

As would be understood to one of skill in the art, the particular biological activity or therapeutic activity that can be tested will vary depending on the particular glycoprotein.

The potential adverse activity or toxicity (e.g., propensity to cause hypertension, allergic reactions, thrombotic events, seizures, or other adverse events) of glycoprotein preparations can be analyzed by any available method. In some embodiments, immunogenicity of a glycoprotein preparation is assessed, e.g., by determining whether the preparation elicits an antibody response in a subject.

In various embodiments, biological activity, therapeutic activity, etc., of a glycoprotein preparation having terminal alpha-galactosyl residues is compared to a glycoprotein preparation lacking terminal alpha-galactosyl residues. In various embodiments, biological activity, therapeutic activity, etc., of a glycoprotein preparation having terminal alpha-galactosyl residues is compared to a glycoprotein preparation having a different level of terminal alpha-galactosyl residues.

Applications

Methods of the present disclosure can be utilized to analyze glycans from glycoproteins in any of a variety of states including, for instance, free glycans, glycoproteins (e.g., glycopeptides, glycolipids, proteoglycans, etc.), cell-associated glycans (e.g., nucleus-, cytoplasm-, cell-membrane-associated glycans, etc.); glycans associated with cellular, extracellular, intracellular, and/or subcellular components (e.g., proteins); glycans in extracellular space (e.g., cell culture medium), etc.

Methods of the present disclosure may be used in one or more stages of process development for the production of a therapeutic or other commercially relevant glycoprotein. Non-limiting examples of such process development stages that can employ methods of the present disclosure include cell selection, clonal selection, media optimization, culture conditions, process conditions, and/or purification procedure. Those of ordinary skill in the art will be aware of other process development stages.

The present disclosure can also be utilized to monitor the extent and/or type of glycosylation occurring in a particular cell culture (e.g., the extent of terminal alpha-galactosyl residues of a glycoprotein preparation produced in the cell culture), thereby allowing adjustment or possibly termination of the culture in order, for example, to achieve a particular desired glycosylation pattern or to avoid development of a particular undesired glycosylation pattern.

The present disclosure can also be utilized to assess glycosylation characteristics of cells or cell lines (e.g., CHO cell lines) that are being considered for production of a particular desired glycoprotein (for example, even before the cells or cell lines have been engineered to produce the glycoprotein, or to produce the glycoprotein at a commercially relevant level).

For example, where the target glycoprotein is a therapeutic glycoprotein, for example having undergone regulatory review in one or more countries, it will often be desirable to monitor cultures to assess the likelihood that they will generate a product with a glycosylation pattern as close to the established glycosylation pattern of the pharmaceutical product as possible (e.g., having a degree of terminal alpha-galactosyl residues which is close to that of the pharmaceutical product), whether or not it is being produced by exactly the same route. As used herein, "close" refers to a glycosylation pattern having at least about a 75%, 80%, 85%, 90%, 95%, 98%, or 99% correlation to the established glycosylation pattern of the pharmaceutical product. In such embodiments, samples of the production culture are typically taken at multiple time points and are compared with an established standard or with a control culture in order to assess relative glycosylation.

For example, in some embodiments, methods for monitoring production of a glycoprotein may comprise steps of (i) during production of a glycoprotein, removing at least first and second glycan-containing samples from the production system; (ii) subjecting each of the first and second glycan-containing samples to an analysis to determine whether a particular modification is present (e.g., terminal alpha-galactosyl residues); and (iii) comparing the products obtained from the first glycan-containing sample with those obtained from the second glycan-containing sample so that differences are determined and therefore progress of glycoprotein production is monitored. In some embodiments, the glycoprotein is abatacept. In some embodiments, the production system comprises CHO cells.

Whether or not monitoring production of a particular target protein for quality control purposes, the present disclosure may be utilized, for example, to monitor glycosylation at particular stages of development, or under particular growth conditions.

In some embodiments, methods described herein can be used to characterize, modulate and/or control or compare the quality of therapeutic products. To give but one example, the present methodologies can be used to assess glycosylation in cells producing a therapeutic protein product. Particularly given that glycosylation can often affect the activity, bioavailability, or other characteristics of a therapeutic protein product, methods for assessing cellular glycosylation during production of such a therapeutic protein product are particularly desirable. Among other things, the present disclosure can facilitate real time analysis of glycosylation in production systems for therapeutic proteins, and hence, modulation of the glycosylation may be achieved.

Representative therapeutic glycoprotein products whose production and/or quality can be monitored in accordance with the present disclosure include, for example, any of a variety of hematologic agents (including, for instance, erythropoietin, blood-clotting factors, etc.), interferons, colony stimulating factors, antibodies, enzymes, and hormones.

Representative commercially available glycoprotein products include, for example, those presented in Table 2, if produced in CHO cells:

TABLE 2

Exemplary Commercially Available Glycoprotein Products

| Protein Product | Reference Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | Bexxar ® |
| antihemophilic factor | Bioclate ™ |
| human growth hormone | BioTropin ™ |
| botulinum toxin type A | Botox ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune Fab, ovine | DigiFab ™ |
| Rasburicase | Elitek ® |
| Etanercept | Enbrel ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | Forteo ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | Hemofil ® |
| Trastuzumab | Herceptin ® |
| Insulin | Humalog ® |
| antihemophilic factor/von Willebrand factor complex-human | Humate-P ® |
| Somatotropin | Humatrope ® |
| human insulin | Humulin ® |
| Adalimumab | HUMIRA ™ |
| recombinant human hyaluronidase | Hylenex ™ |
| interferon alfacon-1 | Infergen ® |
| Eptifibatide | Integrilin ™ |
| alpha-interferon | Intron A ® |
| Palifermin | Kepivance |
| Anakinra | Kineret ™ |
| antihemophilic factor | Kogenate ®FS |
| insulin glargine | Lantus ® |
| granulocyte macrophage colony-stimulating factor | Leukine ®/ Leukine ® Liquid |
| lutropin alfa, for injection | Luveris |
| OspA lipoprotein | LYMErix ™ |
| Ranibizumab | Lucentis ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab (formerly LeuTech ®) | NeutroSpec ™ |
| somatropin [rDNA] | Norditropin ®/ Norditropin |

TABLE 2-continued

Exemplary Commercially Available Glycoprotein Products

| Protein Product | Reference Drug |
|---|---|
| | Nordiflex ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluble fusion protein | Orencia ™ |
| muromomab-CD3 | Orthoclone OKT3 ® |
| human chorionic gonadotropin | Ovidrel ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | Raptiva ™ |
| combination of ribavirin and alpha interferon | Rebetron ™ |
| Interferon beta 1a | Rebif ® |
| antihemophilic factor | Recombinate ® |
| rAHF/ntihemophilic factor | ReFacto ® |
| Lepirudin | Refludan ® |
| Infliximab | Remicade ® |
| Abciximab | ReoPro ™ |
| Reteplase | Retavase ™ |
| Rituximab | Rituxan ™ |
| interferon alfa-2a | Roferon-A ® |
| Somatropin | Saizen ® |
| synthetic porcine secretin | SecreFlo ™ |
| Basiliximab | Simulect ® |
| Eculizumab | Soliris ® |
| Pegvisomant | Somavert ® |
| Palivizumab; recombinantly produced, humanized mAb | Synagis ™ |
| thyrotropin alfa | Thyrogen ® |
| Tenecteplase | TNKase ™ |
| Natalizumab | Tysabri ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In some embodiments, the disclosure provides methods in which glycans from glycoproteins from different sources or samples are compared with one another. In some such examples, multiple samples from the same source (e.g., from the same CHO cell source) are obtained over time, so that changes in glycosylation patterns (and particularly in cell surface glycosylation patterns) (e.g., changes in the presence or extent of terminal alpha-galactosyl residues) are monitored. In some embodiments, one of the samples is a historical sample or a record of a historical sample. In some embodiments, one of the samples is a reference sample.

In some embodiments, the disclosure provides methods in which glycans from glycoproteins expressed by different cell sources are compared with one another. In some embodiments, one or more of the compared cell sources are CHO cells.

In some embodiments, glycans from different cell culture samples prepared under conditions that differ in one or more selected parameters (e.g., cell type, culture type [e.g., continuous feed vs. batch feed, etc.], culture conditions [e.g., type of media, presence or concentration of particular component of particular medium(a), osmolarity, pH, temperature, timing or degree of shift in one or more components such as osmolarity, pH, temperature, etc.], culture time, isolation steps, etc.) but are otherwise identical, are compared, so that effects of the selected parameter on glycosylation are determined. In certain embodiments, glycans from different cell culture samples prepared under conditions that differ in a single selected parameter are compared so that effects of the single selected parameter on glycosylation patterns (e.g., the presence or absence of terminal alpha-galactosyl residues) are determined. Among other applications, therefore, use of techniques as described herein may facilitate determination of the effects of particular parameters on glycosylation patterns in cells.

In some embodiments, glycans from different batches of a glycoprotein, whether prepared by the same method or by different methods, and whether prepared simultaneously or separately, are compared. In such embodiments, the present disclosure facilitates quality control of a glycoprotein preparation. Alternatively or additionally, some such embodiments facilitate monitoring of progress of a particular culture producing a glycoprotein (e.g., when samples are removed from the culture at different time points and are analyzed and compared to one another). In some examples, multiple samples from the same source are obtained over time, so that changes in glycosylation patterns are monitored. In some embodiments, glycan-containing samples are removed at about 30 second, about 1 minute, about 2 minute, about 5 minute, about 10 minute, about 30 minute, about 1 hour, about 2 hour, about 3 hour, about 4 hour, about 5 hour, about 10 hour, about 12 hour, or about 18 hour intervals, or at even longer intervals. In some embodiments, glycan-containing samples are removed at irregular intervals. In some embodiments, glycan-containing samples are removed at 5 hour intervals.

In some embodiments, methods in accordance with the disclosure may be used to monitor the glycosylation pattern of glycoproteins during the course of their production by cells. For example, production of a glycoprotein (e.g., commercial production) may involve steps of (1) culturing cells that produce the glycoprotein, (2) obtaining samples at regular or irregular intervals during the culturing, and (3) analyzing the glycosylation pattern of produced glycoprotein(s) in obtained sample(s). In some embodiments, such methods may comprise a step of comparing the glycosylation patterns of produced glycoprotein(s) in obtained samples to one another. In some embodiments, such methods may comprise a step of comparing glycosylation patterns of produced glycoprotein(s) in obtained sample(s) to the glycosylation pattern of a reference sample.

In any of these embodiments, features of the glycan analysis can be recorded, for example in a quality control record. As indicated above, in some embodiments, a comparison is with a historical record of a prior or standard batch and/or with a reference sample of glycoprotein.

In some embodiments, glycans from different batches of a particular glycoprotein, whether prepared by the same method or by different methods, and whether prepared simultaneously or separately, are compared to one another and/or to a reference sample. In some embodiments, batch-to-batch comparison may comprise the steps of (i) providing a first glycan preparation from a first batch of the glycoprotein; (ii) providing a second glycan preparation from a second batch of the glycoprotein; (iii) subjecting each of the first and second glycan preparations to analysis procedure; and (iv) comparing the results of the analysis obtained from the first glycan preparation with the cleavage products obtained from the second preparation so that consistency of the two batches is assessed. In some embodiments, glycan preparations can be provided by removing at least one glycan from at least one glycoprotein from a batch and, optionally, isolating removed glycans. In some embodiments, glycan preparations may be labeled as described herein (e.g., fluorescently and/or radioactively; e.g., prior to and/or after isolation).

In some embodiments, the present disclosure facilitates quality control of a glycoprotein preparation. Features of the glycan analysis can be recorded, for example in a quality control record. As indicated above, in some embodiments, a comparison is with a historical record of a prior or standard batch of glycoprotein. In some embodiments, a comparison is with a reference glycoprotein sample.

In certain embodiments, the present disclosure may be utilized in studies to modify the glycosylation characteristics of a cell, for example to establish a cell line and/or culture conditions with one or more desirable glycosylation characteristics, e.g., a cell line that produces glycoproteins having, or lacking, terminal alpha-galactosyl residues. Such a cell line and/or culture conditions can then be utilized, if desired, for production of a particular target glycoprotein for which such glycosylation characteristic(s) is/are expected to be beneficial. In particular embodiments, the cell is a CHO cell.

According to the present disclosure, techniques described herein can be used to detect desirable or undesirable glycans, for example to detect or quantify the presence of one or more contaminants in a glycoprotein product, or to detect or quantify the presence of one or more active or desired species.

In certain embodiments, methods described herein facilitate detection of glycans that are present at very low levels in a source (e.g., a biological sample, glycan preparation, etc.). In such embodiments, it is possible to detect and/or optionally quantify the levels of glycans that are present at levels less than about 10%, 5%, 4%, 3%, 2%, 1.5%, 1%, 0.75%, 0.5%, 0.25%, 0.1%, 0.075%, 0.05%, 0.025%, or 0.01% within a population of glycans. In some embodiments, it is possible to detect and/or optionally quantify the levels of glycans comprising between 0.1% and 5%, e.g., between 0.1% and 2%, e.g., between 0.1% and 1% of a glycan preparation.

In some embodiments, methods described herein allow for detection of particular linkages that are present at low levels within a population of glycans. For example, the present methods allow for detection of particular linkages (e.g., terminal gal-α-1,3-gal linkages) that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, or less than 0.01% within a population of glycans.

In some embodiments, methods described herein allow for detection of relative levels of individual glycan species within a population of glycans. For example, the area under each peak of a liquid chromatograph can be measured and expressed as a percentage of the total. Such an analysis provides a relative percent amount of each glycan species within a population of glycans.

The present disclosure will be more specifically illustrated with reference to the following examples. However, it should be understood that the present disclosure is not limited by these examples in any manner.

One of skill in the art may readily envision various other combinations within the scope of the present invention, considering the example with reference to the specification herein provided.

EXAMPLES

Example 1

Orencia™ (abatacept) is a soluble fusion protein that consists of the extracellular domain of human cytotoxic T-lymphocyte-associated antigen 4 (CTLA-4) linked to the modified Fc (hinge, CH2, and CH3 domains) portion of human immunoglobulin G1 (IgG1). Abatacept is produced by recombinant DNA technology in a mammalian cell expression system. The apparent molecular weight of abatacept is 92 kilo Daltons. Abatacept is used to treat the symptoms of rheumatoid arthritis, to slow the progression of joint damage, and to improve physical function. The large complexity of this biotherapeutic arising from its heavy glycosylation (3 N-linked and two O-linked glycosylation sites) requires careful production and characterization. Since different modifications to the protein chemical composition (protein backbone modifications, glycosylation, etc.) can affect the biological function of the glycoprotein, it is important to ensure a good control over the chemical and physical properties of this biotherapeutic during manufacturing.

The Gal-α1-3Gal epitope ("alpha-gal") is not typically found in human proteins and is not expected in CHO derived products. This epitope is typically observed in proteins isolated from pigs and mice. Humans have circulating antibodies against the Galα1-3Gal termini and therefore, it is important to monitor these species in glycoprotein therapeutics and to understand how this relates to process development. This disclosure indicates the presence of the alpha-gal structure in the abatacept (which is expressed in CHO cells).

Procedure Used to Analyze the Glycan Species:

N-glycans were isolated from the drug substance by treatment with PNGASE-F followed by solid phase extraction purification. Glycans were then 2AB labeled and selected fractions were then analyzed by LC-MS-MS. The glycan structures were further confirmed through a combination of exoglycosidases, MALDI-MS, and Lc-MS/MS.

Figure 3:
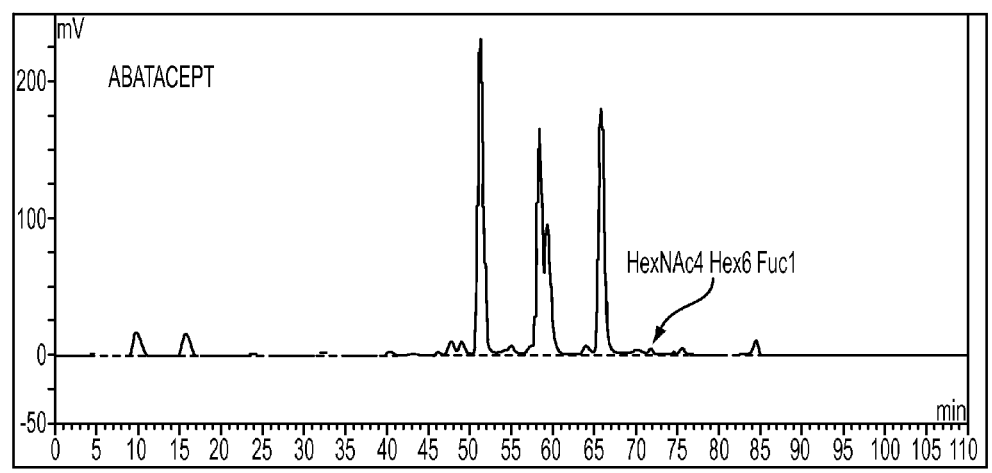
FIG. 3 is a fluorescence chromatogram of a fraction of glycans derived from Abatacept showing the detection of a glycan species with composition $HexNAc_4Hex_6Fuc_1$ that could correspond to a galactose-α-1-3 linked galactose-containing structure.

This data illustrates the presence of the terminal alpha linked galactose in the abatacept-CTLA4 glycoprotein N-glycans. N-linked glycan samples of Orencia™ (abatacept), a soluble fusion protein that consists of the extracellular domain of human cytotoxic T-lymphocyte-associated antigen 4 (CTLA-4) linked to the modified Fc (hinge, CH2, and CH3 domains) portion of human immunoglobulin G1 (IgG1), were analyzed via LC-MS/MS. FIG. 3 shows the fluorescence chromatogram of a fraction of glycans derived from Abatacept showing the detection of a glycan species with composition $HexNAc_4Hex_6Fuc_1$ that could correspond to an galactose-α-1-3galactose-containing structure.

Figure 4:
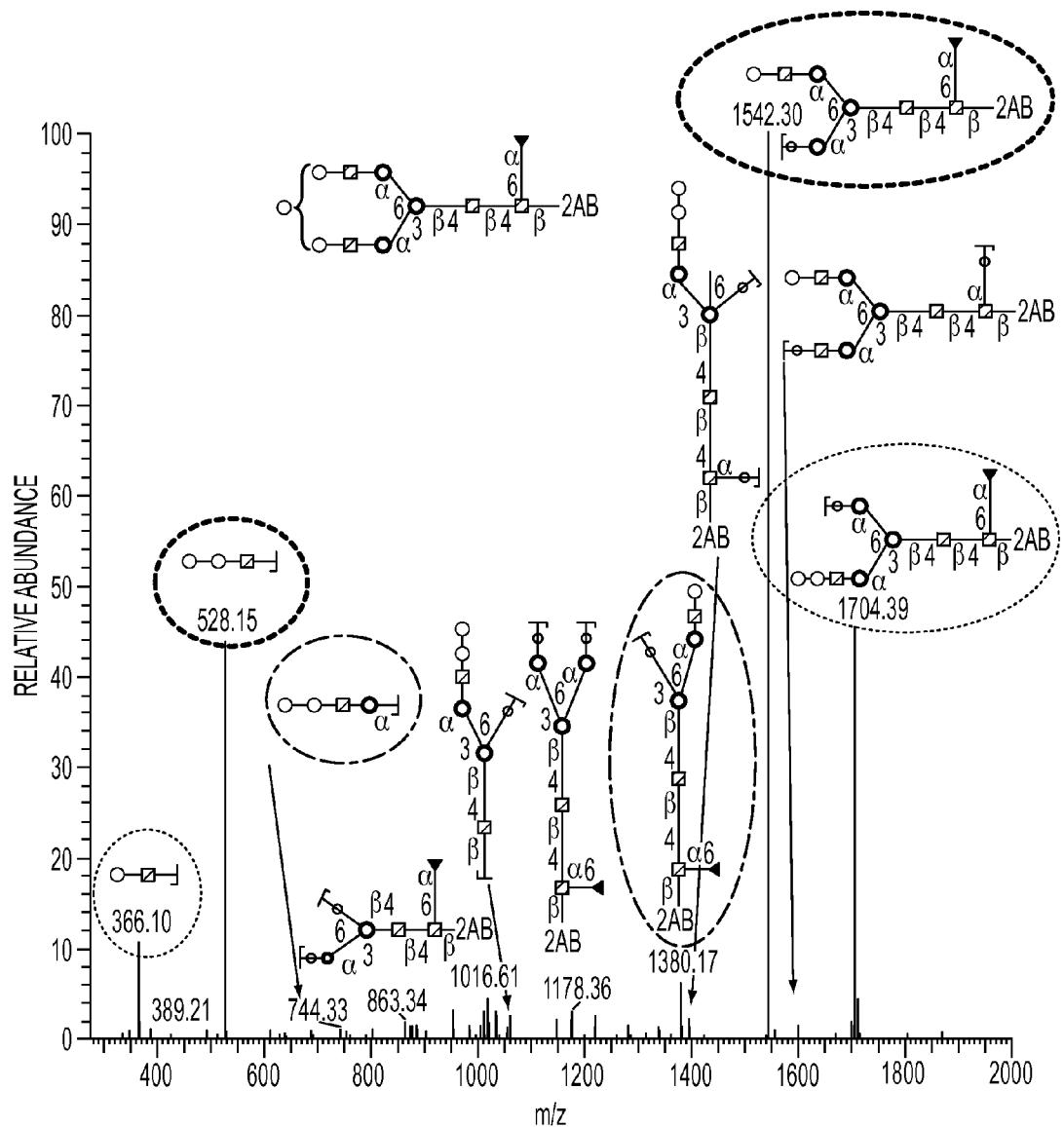
FIG. 4 illustrates the $MS^2$ spectra of a glycan species derived from Abatacept with composition $HexNAc_4Hex_6Fuc_1$. The spectra correlate with a glycan structure containing anon-reducing end galactose-α1-3-galactose.

The $MS^2$ spectrum from the glycan species derived from Orencia™ with composition $HexNAc_4Hex_6Fuc_1$ suggested the presence of the non-reducing end galactose-α-1-3 linked galactose (FIG. 4) although it does not eliminate the possibility of other potential structures such as a hybrid-type glycan.

Figure 5:
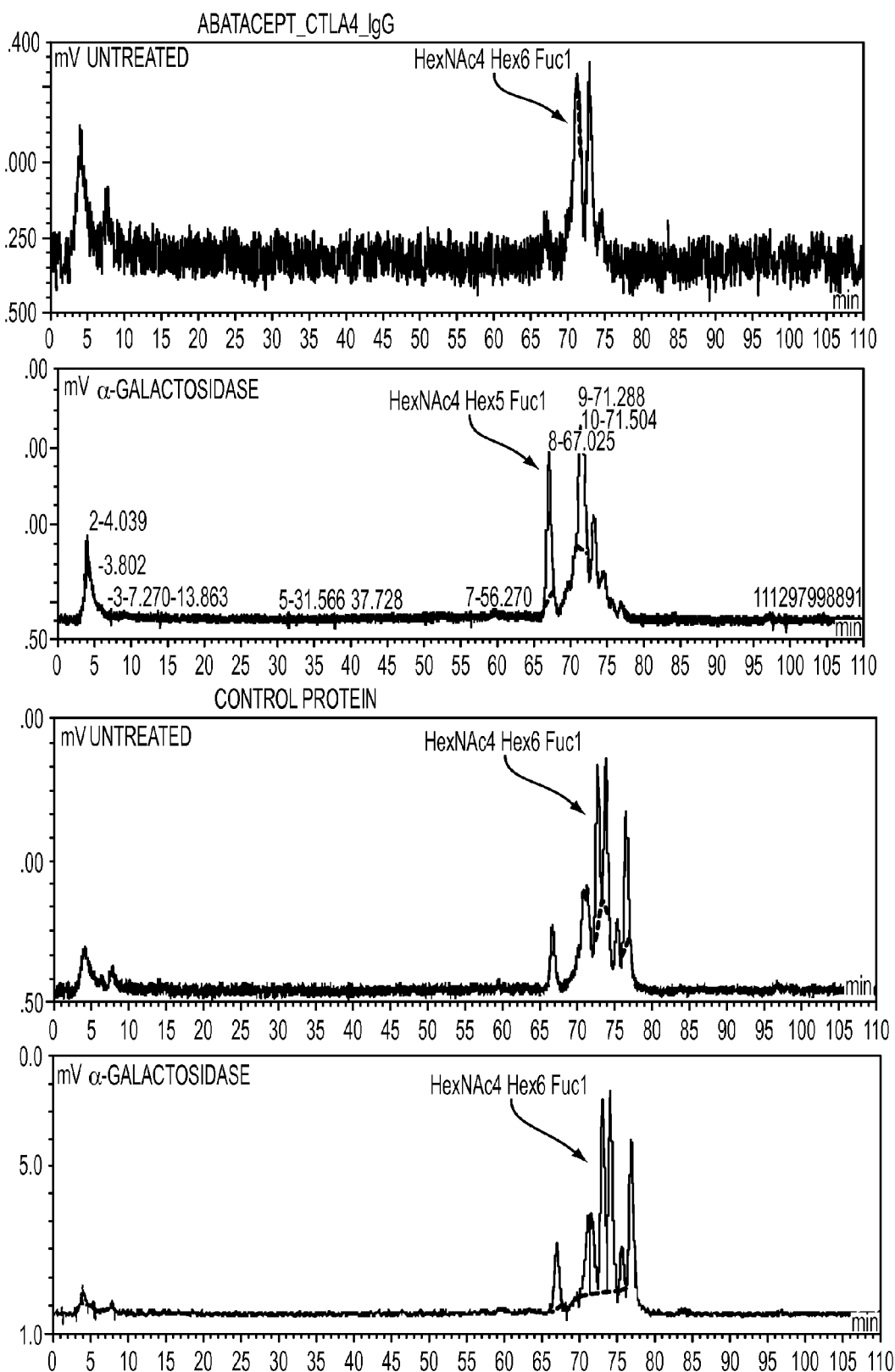
FIG. 5 is a fluorescence chromatogram of a fraction of glycans derived from Abatacept and a control protein (also containing a glycan with composition $HexNAc_4Hex_6Fuc_1$) before and after treatment with α-galactosidase.

Further confirmation of this structure was obtained using a combination of different exoglycosidase treatments followed by LC-ESI-MS/MS and MALDI-MS. N-glycan fractions derived from both Orencia™ and a control protein were subjected to exoglycosidase enzyme treatments. Both samples were treated with (i) α-galactosidase and (ii) a mixture of β-galactosidase, β-N-acetylhexosaminodase, and mannosidase to resolve the potential non-reducing end galactose-α-1-3 linked galactose structure. A comparison of the florescence chromatograms for the products of the two reactions is shown in FIG. 5.

Figure 6:
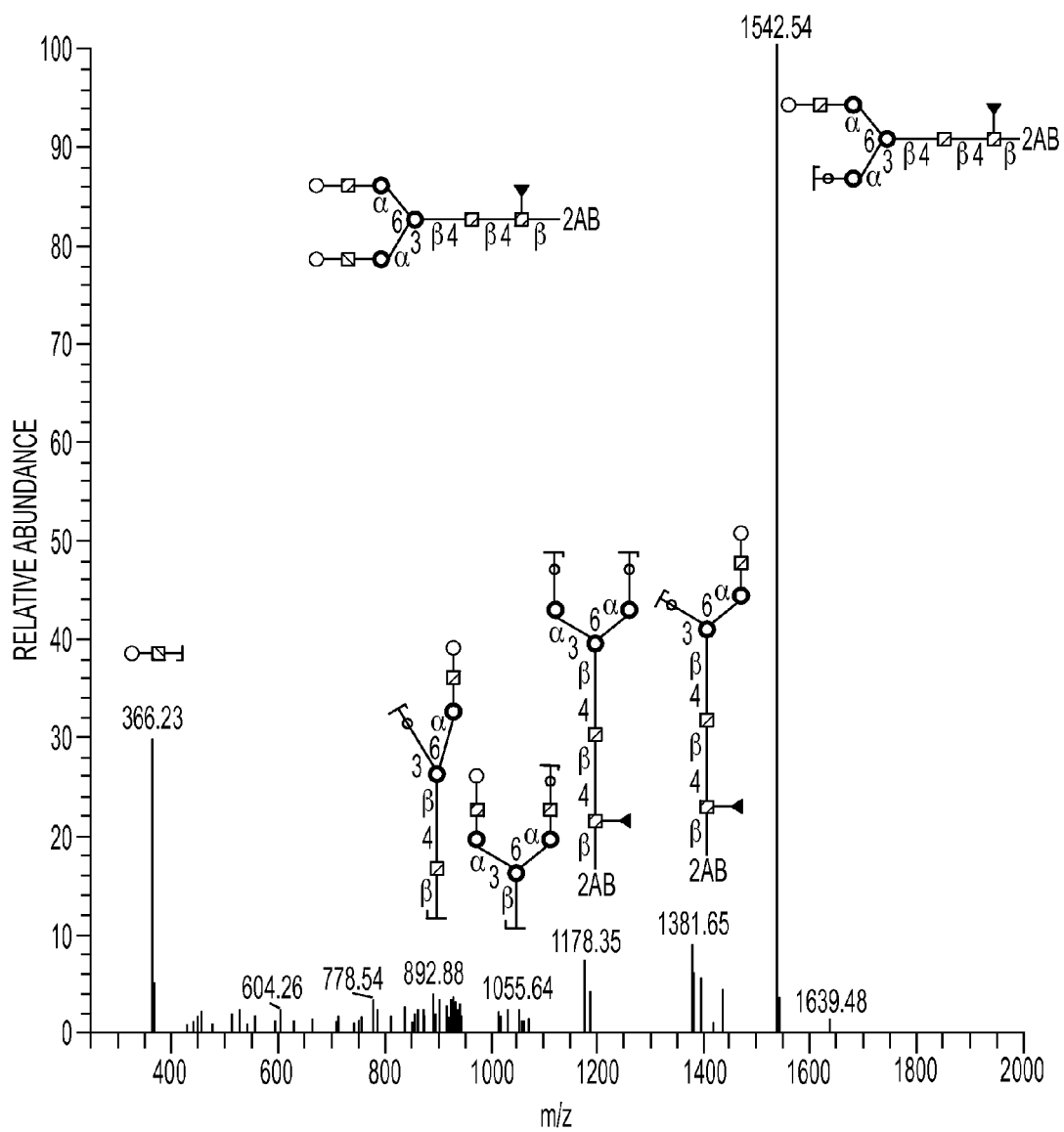
FIG. 6 is an $MS^2$ spectra of the species with composition $HexNAc_4Hex_5Fuc_1$ generated from the treatment of the glycan fraction derived from Abatacept with alpha galactosidase.

No major differences were observed in the glycans from the control protein before and after α-galactosidase treatment. On the other hand, a clear decrease in a species with $HexNAc_4Hex_6Fuc_1$ composition and a concomitant increase in a species $HexNAc_4Hex_5Fuc_1$ composition was observed in Orencia™. The $MS^2$ for the species with $HexNAc_4Hex_6Fuc_1$ composition from abatacept as a result of the enzyme treatment is also shown in FIG. 6.

Figure 7:
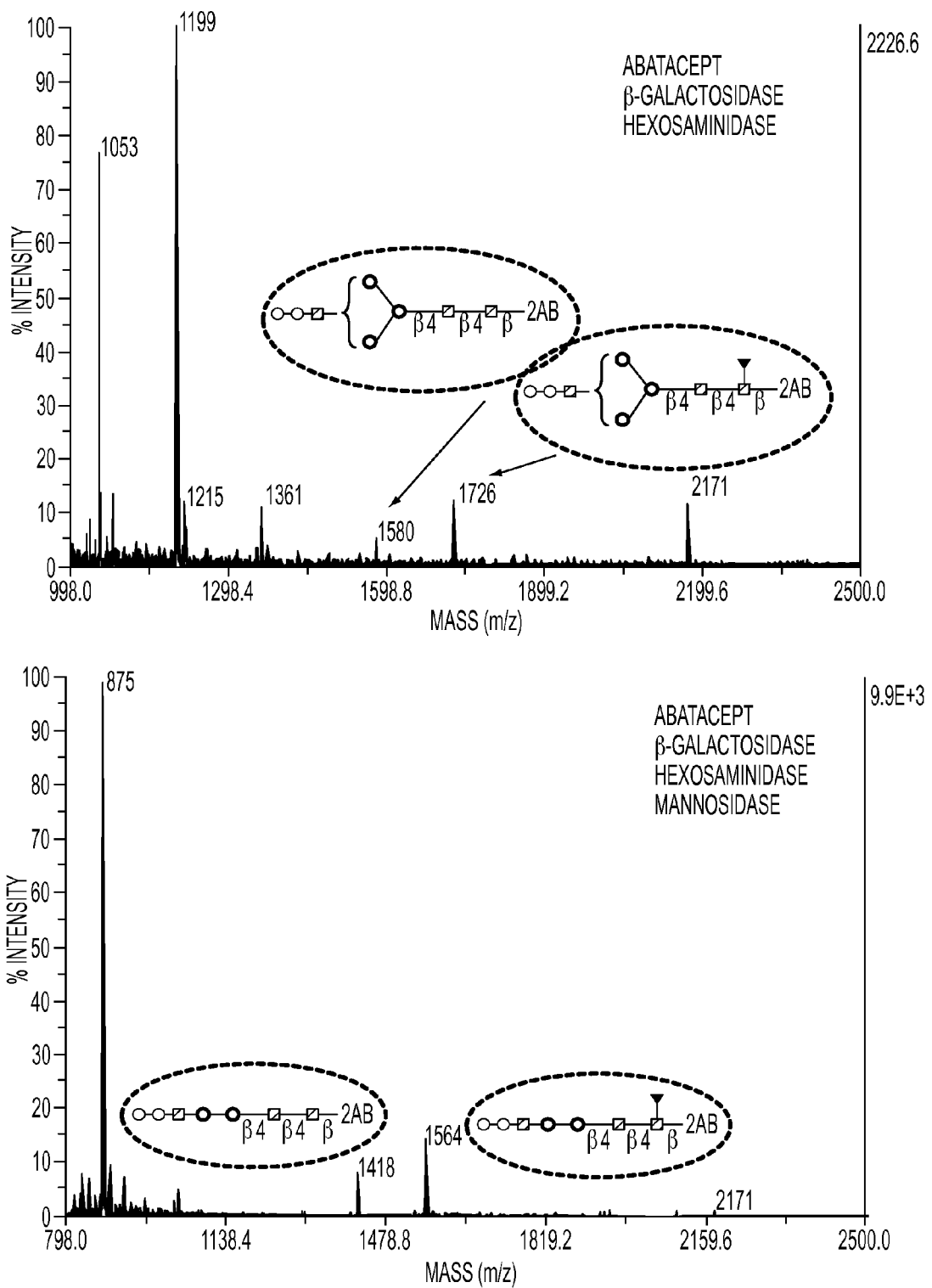
FIG. 7 illustrates a MALDI-MS spectra a fraction of glycans derived from Abatacept treated with different exo-glycosidases.

Additional confirmation was obtained from the results of the treatment with a different set of exoglycosidases (beta-galactosidase, hexosaminidase and mannosidase) as analyzed via MALDI-TOF-MS (FIG. 7).

The data suggests that the species with $HexNAc_4Hex_6Fuc_1$ composition in Orencia™ contains mainly the non-reducing end galactose-α1-3 linked galactose.

Extensions and Alternatives

While the methods has been particularly shown and described with reference to specific illustrative embodiments, it should be understood that various changes in form and detail may be made without departing from the spirit and scope of the present disclosure. Therefore, all embodiments that come within the scope and spirit of the methods, and equivalents thereto, are intended to be claimed. The claims, descriptions and diagrams of the methods, systems, and assays of the present disclosure should not be read as limited to the described order of elements unless stated to that effect.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way. While the methods have been described in conjunction with various embodiments and examples, it is not intended that the methods be limited to such embodiments or examples. On the contrary, the methods encompass various alternatives, modifications, and equivalents, as will be appreciated by those of skill in the art.

The invention claimed is:

1. A method of producing a recombinant therapeutic fusion protein, comprising the steps of:
    (a) culturing Chinese hamster ovary (CHO) cells under conditions suitable for expression of a recombinant therapeutic fusion protein comprising one or more glycans, wherein the CHO cells have not been genetically engineered to produce terminal alpha-galactosyl residues on glycans;
    (b) treating the one or more glycans of the fusion protein with one or more exoglycosidases;
    (c) measuring glycans containing terminal galactose-alpha-1-3-galactose residues on the fusion protein by nuclear magnetic resonance (NMR); and
    (d) producing a recombinant therapeutic fusion protein in the CHO cells if a target level of terminal galactose-alpha-1-3-galactose residues is measured.

2. The method of claim 1, wherein the recombinant therapeutic fusion protein is abatacept.

3. The method of claim 1, wherein the CHO cells are in a cell culture.

4. The method of claim 1, wherein the measuring step is performed on any of: the recombinant therapeutic fusion protein produced by the CHO cells, peptides obtained from the recombinant therapeutic fusion protein produced by the CHO cells, cell surface glycans of the CHO cells, glycan preparations obtained from the CHO cells, glycan preparations obtained from the recombinant therapeutic fusion protein produced by the CHO cells, and combinations thereof.

5. The method of claim 1, wherein the producing step further comprises isolating the recombinant therapeutic fusion protein from the CHO cells.

6. The method of claim 1, wherein the culturing step occurs in a bioreactor.

7. The method of claim 1, wherein the measuring step further comprises use of a technique selected from the group consisting of: chromatographic methods, mass spectrometry (MS) methods, electrophoretic methods, monosaccharide analysis, fluorescence methods, UV-VIS absorbance, enzymatic methods, and combinations thereof.

8. The method of claim 1, wherein the recombinant therapeutic fusion protein is a human recombinant therapeutic fusion protein and in step (d) the CHO cells have been transformed with a vector encoding the human recombinant therapeutic fusion protein.

9. The method of claim 1, wherein the CHO cells are from at least one of: at least two different CHO strains, at least two different clonal cell populations, and at least two different samples from a cell culture in a manufacturing process strain for a fusion protein.

10. The method of claim 1, wherein the CHO cells are from a first CHO cell population and a second CHO cell population and the method further comprises comparing a level of glycans containing terminal galactose-alpha-1-3-galactose residues produced by the first CHO cell population with a level of glycans containing terminal galactose-alpha-1-3-galactose residues produced by the second CHO cell population.

11. The method of claim 1, further comprising comparing a level of glycans containing terminal galactose-alpha-1-3-galactose residues produced by the CHO cells to a reference sample.

12. The method of claim 1, further comprising recording a level of glycans containing terminal galactose-alpha-1-3-galactose residues in a print or computer-readable medium.

13. The method of claim 1, wherein the target level is a quality criterion for a pharmaceutical preparation.

14. The method of claim 1, wherein the target level is a range or value in a product specification.

15. The method of claim 1, wherein the target level is no more than 5% terminal galactose-alpha-1-3-galactose residues.

16. The method of claim 1, wherein the one or more exoglycosidases are selected from the group consisting of sialidase, galactosidase, hexosaminidase, mannosidase, fucosidase, and combinations thereof.

17. The method of claim 1, wherein the treating step comprises treating with one or more exoglycosidases for a time and under conditions suitable for the one or more exoglycosidases to cleave one or more terminal glycosidic bonds from a non-reducing end of the one or more glycans.

* * * * *